United States Patent [19]
Zimmerle

[11] Patent Number: 5,350,694
[45] Date of Patent: Sep. 27, 1994

[54] COMPOSITION METHOD AND DEVICE FOR MEASURING THE DIVALENT CATION CONCENTRATION OR SPECIFIC GRAVITY OF A TEST SAMPLE

[75] Inventor: Chris T. Zimmerle, Elkhart, Ind.

[73] Assignee: Miles Inc., Elkhart, Ind.

[21] Appl. No.: 19,668

[22] Filed: Feb. 19, 1993

[51] Int. Cl.$^5$ .............. G01N 21/00; G01N 31/22; G01N 33/20

[52] U.S. Cl. .................. 436/2; 436/74; 436/79; 436/169; 436/18; 422/56; 422/57; 422/58; 252/408.1; 73/61.42

[58] Field of Search .......... 422/56, 57, 58; 436/2, 436/163, 164, 169, 179, 74, 18; 73/61.41–61.42; 427/2; 252/408.1

[56] References Cited

U.S. PATENT DOCUMENTS

| | | | |
|---|---|---|---|
| 3,754,865 | 8/1973 | Gindler | 436/19 |
| 4,318,709 | 3/1982 | Falb et al. | 422/56 |
| 4,376,827 | 3/1983 | Stiso et al. | 422/56 |
| 4,594,225 | 6/1986 | Arai et al. | 422/56 |
| 4,871,678 | 10/1989 | Wakd et al. | 436/79 |
| 4,871,679 | 10/1989 | Tanaka et al. | 436/79 |
| 5,055,407 | 10/1991 | Lau et al. | 436/2 |
| 5,215,716 | 6/1993 | Arai | 422/56 |

*Primary Examiner*—James C. Housel
*Assistant Examiner*—Rachel Heather Freed
*Attorney, Agent, or Firm*—Roger N. Coe

[57] ABSTRACT

A composition, method and test device for determining the divalent cation concentration or estimating the specific gravity of a test sample are disclosed. The method utilizes a test device comprising a test pad, wherein the test pad includes a carrier matrix incorporating a reagent composition capable of interacting with divalent cations present in the test sample to produce a detectable and measurable response that correlates to the divalent cation concentration or to the specific gravity of the test sample. The reagent composition, comprising a metal-sensitive triphenylmethane dye; a buffer; an optional chelating agent; and suitable carrier, is incorporated into a carrier matrix to provide a test pad of a device useful in a divalent cation assay or a specific gravity assay of a test sample.

19 Claims, No Drawings

5,350,694

COMPOSITION METHOD AND DEVICE FOR MEASURING THE DIVALENT CATION CONCENTRATION OR SPECIFIC GRAVITY OF A TEST SAMPLE

FIELD OF THE INVENTION

The present invention relates to a composition, method and test device for determining the divalent cation concentration or estimating the specific gravity of a test sample. More particularly, the present invention relates to a method of assaying an aqueous test sample, such as urine, for divalent cation concentration or specific gravity by utilizing a reagent composition that undergoes a detectable or measurable response upon contact of the test sample with the reagent composition. The detectable response then is correlated to the divalent cation concentration or the specific gravity of the test sample. The reagent composition provides sufficient sensitivity to test sample divalent cation concentration or specific gravity, and provides sufficient color differentiation between test samples to determine divalent cation concentration or estimate specific gravity of a test sample.

BACKGROUND OF THE INVENTION AND PRIOR ART

The specific gravity of a test sample, such as urine or serum, is a measure of the relative proportions of solid material dissolved in the test sample to the total volume of the test sample. In general, the specific gravity of a test sample is a measure of the relative degree of concentration or the relative degree of dilution of the test sample. The specific gravity of urine can be correlated to the cation concentration, and especially the divalent cation concentration of the urine sample. With regard to urine samples, the assay for specific gravity helps interpret the results of the other assays performed in a routine urinalysis.

Clinically, under appropriate and standardized conditions of fluid restriction or increased fluid intake, the specific gravity of a urine sample measures the concentrating and diluting abilities of the kidneys of an individual. The specific gravity of urine ranges from about 1.005 to about 1.030, and usually is in the range from about 1.010 to about 1.025. A specific gravity of about 1.025 or above in a random first morning urine specimen indicates a normal concentrating ability of the kidneys.

Either an abnormally low or an abnormally high urine specific gravity is clinically significant. Therefore, accurate and reliable specific gravity assays of urine and other aqueous test samples must be available for both laboratory and home use. The assays must permit the accurate measurement of abnormally low and abnormally high specific gravities, such that a correct diagnosis can be made and correct medical treatment implemented, monitored and maintained.

For example, diabetes insipidus, a disease caused by the absence of, or impairment to, the normal functioning of the antidiuretic hormone (ADH), is the most severe example of impaired kidney concentrating ability. This disease is characterized by excreting large urine volumes of low specific gravity. The urine specific gravity of individuals suffering diabetes insipidus usually ranges between 1.001 and 1.003. Low urine specific gravity also occurs in persons suffering from glomerulonephritis, pyelonephritis, and various other renal anomalies. In these cases, the kidney has lost its ability to concentrate the urine because of tubular damage.

An abnormally high urine specific gravity also is indicative of a diseased state. For example, the urine specific gravity is abnormally high in an individual suffering from diabetes mellitus, adrenal insufficiency, hepatic disease or congestive cardiac failure. Urine specific gravity likewise is elevated when an individual has lost an excessive amount of water, such as with sweating, fever, vomiting, and diarrhea. In addition, abnormally high amounts of nonionic urinary constituents, like glucose and protein, increase the urine specific gravity to 1.050 or greater in some individuals suffering from diabetes mellitus or nephrosis. Furthermore, urine with a fixed low specific gravity of approximately 1.010 that varies little from specimen to specimen is known as isothenuric. This condition is indicative of severe renal damage with disturbance of both the concentrating and diluting abilities of the kidney.

Therefore, in order to determine if an individual has either an abnormally high or an abnormally low urine specific gravity, and in order to help monitor the course of a medical treatment to determine its effectiveness, simple, accurate and inexpensive specific gravity assays have been developed. In general, the specific gravity of a test sample is a measurement that relates to the density of the test sample. The specific gravity is a value derived from the ratio of the weight of a given volume of a test sample, such as urine, to the weight of the same volume of water under standardized conditions (Eq. 1).

$$\text{Sp. Gr.} = \frac{\text{weight of urine}}{\text{weight of water}} \qquad \text{Eq. 1}$$

Water has a specific gravity of 1.000. Since urine is a solution of minerals, salts, and organic compounds in water, the specific gravity of urine is greater than 1.000. The relative difference reflects the degree of concentration of the urine specimen and is a measure of the total solids in urine.

Several methods are available to determine the specific gravity of urine. The most widely used method, and possibly the least accurate, employs a urinometer. The urinometer is a weighted, bulb-shaped instrument having a cylindrical stem containing a scale calibrated in specific gravity readings. The urinometer is floated in a cylinder containing the urine sample, and the specific gravity of the urine is determined by the depth the urinometer sinks in the urine sample. The specific gravity value is read directly from the urinometer scale at the junction of the urine with the air. The urinometer method is cumbersome and suffers from the disadvantages of a) requiring large volumes of urine test sample, b) a difficult and inaccurate reading of the urinometer scale, and c) unreliable assays because the urinometer is not regularly recalibrated.

Refractometry provides an indirect method of measuring the specific gravity of urine. The refractive index of urine is directly related to the number of dissolved particles in urine and, therefore, is directly related to the specific gravity of urine. Consequently, measurement of the refractive index of urine can be correlated to the specific gravity of urine. The refractometer method of determining urine specific gravity is desirable because specific gravity measurements are performed on as little as one drop of urine. However, the refractometer has the disadvantages of requiring daily calibration and not being amenable to home assays.

A third urinalysis method for specific gravity, the falling drop method, like the urinometer, is a direct measurement of urine specific gravity. In this method, a drop of urine is introduced into each of a series of columns filled with solvent mixtures of increasing and known specific gravity. When the drop of urine comes to rest after its initial momentum has dissipitated, and then neither rises nor falls, the specific gravity of the urine is determined to be identical to the specific gravity of the solvent mixture of that particular column. The falling drop method, however, is not widely used in routine urinalysis because of the lengthy time requirements in setting up such a assay and the inability of an individual to perform the assay at home.

The falling drop method described above also can be performed instrumentally. The instrument-based assay uses a specially designed column filled with a silicone oil having a controlled specific gravity and viscosity. The column is designed to measure the time required for a precisely measured drop of test sample to fall a distance defined by two optical gates (lamp-phototransistor pairs) mounted one above the other in a temperature-controlled column filled with a water-immiscible silicone oil of a slightly lower density than the test sample. The falling time is measured electronically and computed into specific gravity units. This specific gravity method is very precise, however, the cost of the assay instrument and the degree of skill required to operate the instrument makes home testing for urine specific gravity impractical.

Not one of the above-described specific gravity assay methods is suited to performing specific gravity assays outside a medical office or laboratory. Consequently, reagent impregnated test strips were developed to perform specific gravity assays at home. In general, the test strip assay developed for specific gravity determinations is an indirect assay method, wherein the test strip changes color in response to the ionic strength of the urine sample.

The present day specific gravity test strips comprise a carrier matrix impregnated with a reagent composition including a polyelectrolyte, such as a partially neutralized poly(methyl vinyl ether/maleic acid); a chromogenic indicator, such as bromothymol blue; and suitable buffering agents. The reagent composition is sensitive to the number of ions, or electrolytes, in the urine sample, such that the polyelectrolyte of the reagent composition undergoes a $pK_a$ (acid dissociation constant) change in relation to the ionic strength of the urine sample. Therefore, as the concentration of electrolytes in the urine increases (high specific gravity), the $pK_a$ of the polyelectrolyte present in the reagent composition decreases because free carboxyl groups are converted to carboxylate groups. The overall result is a pH decrease and a color transition of the bromothymol blue chromogenic indicator from blue-green to green to yellow-green in response to increased specific gravity. The resulting color transition, indicating a pH change caused by increasing ionic strength, i.e., increasing specific gravity, is empirically related to the specific gravity of the test sample.

For test strips utilizing the partially neutralized poly(methyl vinyl ether/maleic acid) polyelectrolyte and bromothymol blue indicator, assays for specific gravity are performed on aqueous test samples having a specific gravity ranging from 1.000 to 1.030. A reading of 1.000, or a blue-green color, indicates that the urine has a very low specific gravity, as demonstrated by the lack of a color transition of the chromogenic indicator dye. A specific gravity reading of from 1.005 to 1.030 is signified by color transitions, of from blue-green through green to yellow-green, that serve as reliable indicators of increasing specific gravity.

It would be extremely advantageous to have a simple and trustworthy method of semiquantitatively assaying for urine specific gravity that allows visual differentiation of specific gravity values within the range of 1.000 to about 1.050. By providing a semiquantitative method of determining urine specific gravity in an easy to use form, such as a dip-and-read test strip, the urine assay can be performed by laboratory personnel to afford immediate test results. The specific gravity assay results can be interpreted in conjunction with assays for other urine constituents, such that a diagnosis can be made without having to wait for assay results and medical treatment can be commenced immediately. Furthermore, the test strip method can be performed by an individual at home to estimate the specific gravity of the urine and therefore to help monitor the success of the medical treatment the individual is undergoing.

As will be described more fully hereinafter, the method of the present invention allows the fast and trustworthy assay for the divalent cation concentration or the specific gravity of urine by utilizing a test strip having a test pad that incorporates a reagent composition comprising a metal-sensitive triphenylmethane (MSTPM) dye. The reagent composition undergoes a color transition in response to the divalent cation concentration of the test sample. The color transition is directly related to the divalent metal ion concentration. Therefore, the reagent composition including the MSTPM dye provides sufficient assay sensitivity to allow the quantitative determination of divalent cation concentration and the semiquantitative determination of specific gravity.

Any method of assaying for the divalent cation concentration or the specific gravity of urine or other aqueous test samples must yield trustworthy and reproducible results by utilizing a reagent composition that undergoes a color transition due to an interaction in response to the divalent cation concentration or to the specific gravity of the test sample, and not as a result of a competing chemical or physical interaction, such as a pH change or preferential interaction with another test sample component, like protein or glucose. Additionally, the method and composition utilized in the divalent cation assay or specific gravity assay should not adversely affect or interfere with the other test reagent pads that are present on multiple test pad strips.

In accordance with the present invention, a reagent composition incorporated into the carrier matrix significantly reduces the development of an interfering background color, and thereby provides a sufficient sensitivity and color differentiation to assay for divalent cation concentration quantitatively, or for specific gravity semiquantitatively, especially in the range of about 1.000 to about 1.015. In addition, although dry phase test strips have been used to assay for specific gravity, no dry phase test strip has incorporated an MSTPM dye to provide sufficient sensitivity and sufficient visual color resolution to allow the assay of divalent cation concentration, or to allow the semiquantitative specific gravity assay of a test sample.

The prior art contains references to the polyelectrolyte-dye chemistry utilized in the above-discussed specific gravity assay of urine. For example, Falb et al. U.S. Pat. No. 4,318,709 and Stiso et al. U.S. Pat. No. 4,376,827 disclose the basic polyelectrolyte-dye technique used to assay for urine specific gravity. Both patents teach utilizing polyelectrolyte-dye chemistry to determine the specific gravity of urine by monitoring the color transition of the dye.

However, the present invention provides a composition and method for the accurate determination of divalent cation concentration, or the semiquantitative determination of specific gravity, of urine and other aqueous test samples by utilizing an MSTPM dye as the indicator component of a reagent composition in the absence of a polyelectrolyte. European Patent Application 0 349 934 discloses a test strip and method of determining specific gravity or ionic strength of a sample utilizing a composition including a buffer, a complex former and a pH indicator dye. The complex former can be a crown ether, a cryptand, a podand or a multifunctional liquid. The pH indicator dye is a standard dye, such as bromothymol blue or thymol blue. European Patent Application 0 349 934 does not teach or suggest an MSTPM dye utilized in the present invention.

Greyson et al., in U.S. Pat. No. 4,015,462, disclose a support matrix incorporating osmotically-friable microcapsules containing a fluid including a dye. A portion of the microcapsules bursts upon contact with a test sample of low osmolality. A resulting release of the dye-containing fluid causes a color transition that is correlated to the specific gravity. However, the difficult production of the microencapsulated-containing supporting matrix is a serious disadvantage of the Greyson et al. method.

In contrast to the prior art, and in contrast to the presently available commercial test strips, the method of the present invention provides increased sensitivity in the measurement of urine divalent cation concentration, and provides a semiquantitative measurement of urine specific gravity, by utilizing a reagent composition including a MSTPM dye, a buffer, and optionally a chelating agent, wherein the reagent composition is essentially free of polyelectrolytes. The present reagent composition effectively reduces the development of a background color in the test pad thereby either providing a semiquantitative specific gravity assay, or providing an accurate determination of divalent cation concentration. Hence, new and unexpected results are achieved in the dry phase reagent strip assay of urine and other aqueous test samples for divalent cation concentration or for specific gravity.

SUMMARY OF THE INVENTION

In brief, the present invention is directed to a new and improved method and composition for determining the divalent cation concentration or estimating the specific gravity of an aqueous test sample, and especially the divalent cation concentration or the specific gravity of a biological fluid, such as urine, perspiration, and serum. The method includes using a reagent composition capable of interacting with a test sample to produce a detectable and measurable response that can be correlated to the divalent cation concentration or the specific gravity of the test sample. For home use, the reagent composition produces a visually detectable response. For laboratory use, the reagent composition produces a response that is detectable visually or instrumentally.

The method is suitable for dry phase assays, wherein the reagent composition is incorporated into a carrier matrix to provide a test pad of a test device. The carrier matrix of the test pad comprises a bibulous porous material, like filter paper, or a nonbibulous porous material, like a glass fiber or a permeable layer of a polymeric material. The reagent composition is homogeneously incorporated into the carrier matrix, and the carrier matrix then holds the reagent composition homogeneously throughout the carrier matrix in a known concentration while maintaining carrier matrix penetrability for the liquid test sample.

More particularly, the present invention is directed to a method of assaying for the divalent cation concentration or the specific gravity of urine and other biological or aqueous test samples by utilizing a new reagent composition. It has been demonstrated that a reagent composition including a metal-sensitive triphenylmethane dye, i.e., an MSTPM dye, provides a sufficient sensitivity to test sample divalent cation concentration, and a sufficient color differentiation between test samples of different specific gravity, to permit the accurate measurement of the divalent cation concentration or the semiquantitative measurement of the specific gravity of the test sample.

In accordance with an important feature of the present invention, the specific gravity of urine and other test samples can be determined, semiquantitatively, between about 1.000 and about 1.050, and especially between about 1.000 and about 1.015. By including an MSTPM dye in the reagent composition of the present invention, the presence of a polyelectrolyte is obviated, and the assays are more accurate because the development of an interfering background color is substantially reduced. Accordingly, an improved sensitivity to divalent cation concentration is achieved by utilizing the present reagent composition. Surprisingly and unexpectedly, the present reagent composition, including an MSTPM dye, allows the accurate measurement of divalent cations, like calcium and magnesium, in urine and other test samples. In accordance with another important feature of the present invention, the pH of the reagent composition can be adjusted to assay for calcium ion or for total calcium ion and magnesium ion.

Therefore, one aspect of the present invention is to provide a new and improved method and composition for measuring the divalent cation concentration or the specific gravity of an aqueous liquid. The new composition interacts with an aqueous test sample to produce a visible change, such as a change in color of a test device, that is indicative of the specific gravity or the divalent cation concentration of the test sample.

Another aspect of the present invention is to provide a method of assaying urine or other aqueous test samples that substantially reduces the development of a background color and provides sufficient sensitivity and sufficient visual color resolution to allow differentiation between, and the semiquantitative measurement of, specific gravities.

Another aspect of the present invention is to provide a method of assaying urine or other aqueous test samples utilizing a reagent composition that can interact with divalent cations present in urine or other aqueous test sample, and undergo a detectable and measurable color transition to establish the divalent cation concentration or estimate the specific gravity of the test sample.

Another aspect of the present invention is to provide a reagent composition that interacts with the divalent cations of the test sample and undergoes a visually or instrumentally differentiable color transition to allow the determination of test sample total divalent cation concentration or calcium ion concentration, or to allow the semiquantitative determination of test sample specific gravity in the range of about 1.000 to about 1.050, and especially about 1.000 to about 1.015.

Another aspect of the present invention is to provide a method of assaying for the divalent cation concentration or the specific gravity of a liquid test sample by incorporating a reagent composition into a dry phase detection device, wherein the reagent composition comprises: (a) an MSTPM dye, like cresolphthalein complexone; (b) a buffer; (c) and a suitable carrier, and wherein the reagent composition is essentially free of a polyelectrolyte. In a preferred embodiment the reagent composition includes, optionally, (d) a chelating agent.

Still another aspect of the present invention is to provide a new method of assaying for the divalent cation concentration or the specific gravity of an aqueous test sample by utilizing a test device including a carrier matrix having incorporated therein a reagent composition capable of interacting with divalent cations present in the test sample, wherein the carrier matrix comprises a bibulous matrix, like filter paper, or a nonbibulous matrix, like a glass fiber or a layer of a permeable polymeric material.

A further aspect of the present invention is to provide an improved dry phase test strip that incorporates a reagent composition comprising an MSTPM dye into the carrier matrix, and thereby provides an assay of new and unexpected precision and selectively in response to the divalent cation concentration of a test sample.

The above and other aspects and advantages and novel features of the present invention will become apparent from the following detailed description of the invention.

DETAILED DESCRIPTION OF THE INVENTION

In accordance with the method of the present invention, the assay of aqueous test samples for divalent cation concentration, or for specific gravity, is accomplished by utilizing a reagent composition that is essentially free of a polyelectrolyte and that includes an MSTPM dye. By employing a reagent composition including an MSTPM dye in a sufficient concentration and at a proper pH, sufficient sensitivity and sufficient visual color differentiation between test samples of differing divalent cation concentrations are achieved. Therefore, the accurate, reproducible divalent cation concentration assay of aqueous test samples is provided. The composition and method also can be used to semiquantitatively determine test sample specific gravity because specific gravity can be correlated to divalent cation concentration. The sensitivity and color resolution to test sample divalent cation concentration and specific gravity afforded by the method of the present invention are especially useful in urine assays. The method also is useful in numerous water testing applications, such as for total hardness or calcium hardness.

Present day commercial test strip assays effectively measure specific gravities between about 1.000 and about 1.050. Present-day test strips are not capable of assaying for calcium ion concentration or total divalent cation concentration. Such assays are important to individuals that are prone to forming kidney stones. To date, such assays have been performed by ion specific electrodes. However, the present composition and method allow an individual to test for divalent cation concentration at home with a test strip.

The present invention also allows the semiquantitative assay of test sample specific gravity because specific gravity can be correlated to divalent cation concentration. The semiquantitative assay for urine specific gravity is clinically important because the urine specific gravity assay is interpreted in conjunction with assays for other urine analytes to assist in diagnosing a diseased state. The present invention is especially useful in assaying a urine sample having a specific gravity of about 1.000 to about 1.015. For urine specific gravities within the relatively normal range of from about 1.010 to about 1.025, the method of the present invention still affords sufficient color differentiation and sufficient sensitivity to urine specific gravity. However, clinical benefits are realized in this normal specific gravity range by interpretation of the specific gravity assay in conjunction with urine assays for other analytes, such that all of the assays can provide information concerning an abnormal physiological state that must be investigated further.

It will become apparent that in addition to assaying urine, the method and composition of the present invention also can be used to determine the divalent cation concentration and specific gravity of blood plasma and serum; and more generally, the divalent cation concentration and specific gravity of many other physiological fluids, like perspiration, as well. The composition and method of the present invention also can assay liquid test samples, like water samples, for divalent metal concentration within predetermined ranges. Adjustment of reagent composition pH allows either the selective measurement of calcium ion concentration or the measurement of all divalent cation species in the test sample.

To achieve the full advantage of the present invention, the method and composition are employed in dry phase, test pad assays to determine the divalent cation concentration or the specific gravity of urine or other aqueous test samples. A dry phase test strip, including a test pad comprising a carrier matrix incorporating a reagent composition of the present invention, allows the rapid semiquantitative assay of urine specific gravity by visual means. In addition, by a judicious selection of the amounts of ingredients present in the reagent composition and of pH, a dry phase test strip can be used to determine the divalent cation concentration, such as calcium ion concentration or total divalent cation concentration, in aqueous solution, within predetermined ranges.

In particular, the present invention allows determination of divalent cation concentration or the specific gravity, of a test sample by a visual color change of a test pad on a test strip. Test sample specific gravity is determined by semiquantitatively correlating the divalent cation concentration of the test sample to test sample specific gravity. The test strip includes a test pad comprising an inert carrier matrix incorporating a reagent composition comprising a sufficient amount of buffered MSTPM dye. The MSTPM dyes include at least one carboxyl group substituent on each of the "B" and "C" aromatic rings of the MSTPM dye and are capable of complexing with divalent cations.

MSTPM dyes useful in the present invention have the general structural formula (I):

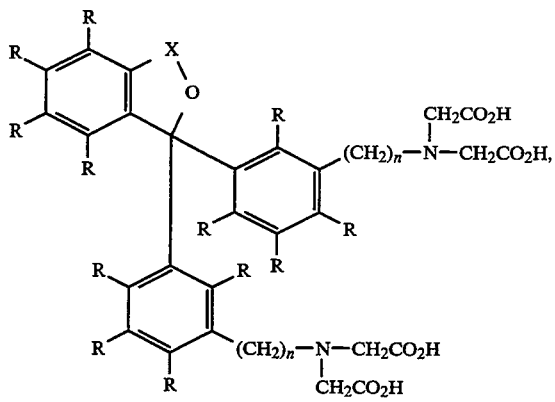

(I)

wherein X is carbonyl (C=O) or sulfonyl (O=S=O), n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate. As will be demonstrated in more detail hereinafter, a particularly useful MSTPM dye having the general structural formula (I) is o-cresolphthalein complexone.

The present composition and method allow the rapid colorimetric determination of the divalent cation concentration or the specific gravity of a test sample. Previous specific gravity assay methods employed indicator dyes that are sensitive to pH and polyelectrolytes. Assay methods for divalent cation concentration utilized ion specific electrodes. The present method is essentially insensitive to the pH normally encountered in urine samples because a sufficient amount of a buffer is included in the reagent composition, without exerting an adverse affect on assay sensitivity.

The pH indicator dyes conventionally used in specific gravity assays undergo color transitions due to a $pK_a$ (acid dissociation constant) change in a polyelectrolyte, such as a partially neutralized poly(methyl vinyl ether/maleic acid), upon contacting urine of different ionic strengths, or specific gravities. The phenomena is fully described in Falb et al. U.S. Pat. No. 4,318,709 and Stiso et al. U.S. Pat. No. 4,376,827, wherein the various dyes, the polyelectrolytes and the buffers required to observe the $pK_a$ change are disclosed. The Falb et al. and Stiso et al. patents basically describe the present day dry phase test strips employed to assay for the specific gravity of urine. These test strips generally include: (a) an indicator dye that normally undergoes a color transition in the neutral pH range of about 6 to about 8, such as bromothymol blue; and (b) a partially neutralized polyelectrolyte.

The $pK_a$ of the partially neutralized polyelectrolyte decreases as the ionic strength of the urine increases. The overall result is a drop in pH, and the bromothymol blue indicator changes color from blue-green to green to yellow-green in response to the pH change caused by increasing ionic strength. The increase in ionic strength of an aqueous test sample is directly related to an increase in specific gravity; the color transition of the dye therefore is empirically related to specific gravity values. This present day method allows specific gravities to be determined to within about 0.005. The present day method suffers from the disadvantage of color transition instability, wherein the color transition fades over a time period of minutes. Accordingly, the accuracy of the results is technique dependent.

In accordance with an important feature of the present invention, an interfering background color can be substantially reduced by selecting a properly buffered pH and by optionally incorporating a strong chelating agent into the reagent composition. Reducing the buffered pH inhibits the binding ability of the MSTPM dyes to divalent cations. Including an optional chelating agent, such as ethylenediaminetetraacetic acid (EDTA), introduces a compound that preferentially complexes to the divalent cations over the MSTPM dye. When the divalent cation concentration rises above the concentration of the chelating agent, then binding of the divalent cation to the MSTPM dye reoccurs. As will be discussed more fully hereinafter, surprisingly and unexpectedly, a reagent composition, including a sufficient amount of a properly buffered MSTPM dye and an optional chelating agent, essentially eliminates the development of an interfering background color, provides improved and increased sensitivity to test sample divalent cation concentration and specific gravity, and provides improved visual color differentiation between test samples of differing specific gravity.

The Falb et al. and Stiso et al. patents disclose a composition and a method wherein the ionic strength of the test sample induces a change in the $pK_a$ of the polyelectrolyte. The change in $pK_a$ is detected by a pH change and a pH indicator. Accordingly, in the previously disclosed methods no direct interaction between the indicator dye and the polyelectrolyte occurs. The composition and method of the present invention differ from the above disclosures in that a divalent cation interacts directly with the MSTPM dye, and an observable color change results. No intermediate compounds, like a polyelectrolyte, are required. A color transition results from a direct interaction between divalent cations and the MSTPM dye.

A buffer is included in the composition of the present invention in a sufficient amount to counteract the buffer capacity of urine, and essentially no reduction in the sensitivity of the MSTPM dye to test sample divalent cation concentration or specific gravity is observed. Using an MSTPM dye in a reagent composition to determine the divalent cation concentration, or the specific gravity, of a test sample provides a trustworthy assay of an aqueous test sample. In addition to reliable assays, the method of the present invention provides rapid assay results. Therefore, the present method and composition provide reproducible and trustworthy divalent cation concentration or specific gravity assays which are performable at home or in the laboratory to yield essentially immediate assay results.

The method of the present invention utilizes the color transition occurring as a result of a direct interaction between the MSTPM dye and the divalent cations present in the test sample to assay for divalent cation concentration or to semiquantitatively assay for specific gravity. The use of a MSTPM dye as the indicator component of a reagent composition allows the divalent cation concentration of test liquids to be accurately and reliably measured, such that the divalent cation concentration can be correlated, semiquantitatively, to test liquid specific gravity. In accordance with an important feature of the present invention, the MSTPM dye of the reagent composition interacts directly with the divalent cations present in the test sample to provide a differentiable color transition. The direct interaction has sufficient assay sensitivity and sufficient color resolution between test samples of different divalent cation concentration and specific gravity and occurs upon interaction between the MSTPM dye and the divalent cations present in the test sample to provide an accurate measurement of test sample divalent cation concentration and a semiquantitative measurement of test sample specific gravity.

Therefore, the reagent composition of the present invention comprises: (a) an MSTPM dye, (b) a buffer, and (c) a suitable carrier. The reagent composition optionally includes (d) a chelating agent. The reagent composition is used in a method, such as in a dry phase test strip method, to assay a test sample, like urine, for divalent cation concentration or specific gravity.

The MSTPM dye utilized in the present invention is depicted by general structural formula (I):

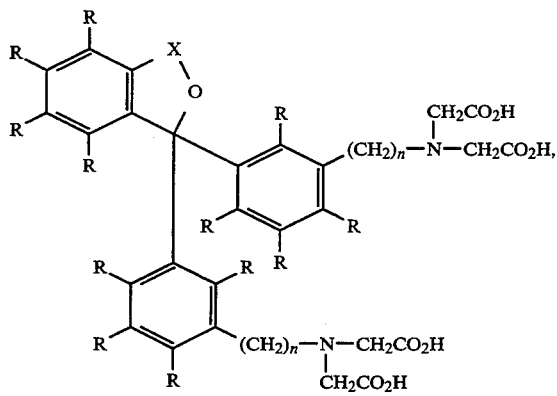

wherein X is carbonyl (C=O) or sulfonyl (O=S=O), n is a number from 0 to about 3, and the R substituents are selected, independently, from the group consisting of hydrogen, hydroxy, an alkyl group including one to about 5 carbon atoms, bromo, chloro, fluoro, iodo, sulfonate, and phosphate.

In general, the useful MSTPM dyes, as depicted in general structural formula (I), can be essentially any phenolphthalein-type dye or phenolsulfonephthalein-type dye that includes a carboxyl group substituent, like a carboxylated amino substituent, on both the "B" and the "C" aromatic rings of the MSTPM dye and that is capable of complexing with divalent cations. Such MSTPM dyes, after complexing with divalent cations present in the test sample, undergo a color transition in response to complexing with the divalent metal cations. The degree and intensity of the color transition are directly related to the concentration of divalent cations in the test sample; and the concentration of the divalent cations is directly related to the specific gravity of the test sample. Therefore, the degree and intensity of the color transition are correlated to the specific gravity of the test sample.

The particular MSTPM dye selected as the dye component of the reagent composition can be determined by those skilled in the art of designing test kits in order to provide a divalent cation concentration assay or a specific gravity assay having maximum visual color resolution and maximum sensitivity. The MSTPM dye included in the present reagent composition can be prepared by methods well known to persons skilled in the art. Furthermore, several MSTPM dye compounds useful in the method of the present invention are well known dyes that are presently available commercially.

The MSTPM dye is present in the reagent composition at a concentration of about 5 mM (millimolar, or millimoles per liter) to about 60 mM, and preferably from about 10 mM to about 50 mM. To achieve the full advantage of the present invention, the MSTPM dye is present in the reagent composition at a concentration of about 15 mM to about 40 mM.

A particularly useful MSTPM dye is cresolphthalein complexone having the structural formula (II):

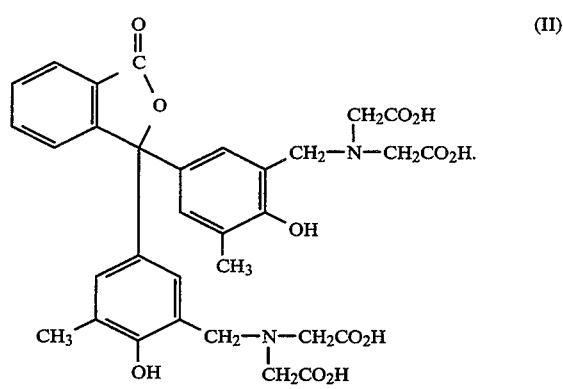

The dye compound of structural formula (II) exhibits an excellent ability to complex with divalent cations, like magnesium and calcium ions, and, as a result, undergo a detectable and differentiable color transition. Other complexones that include at least one carboxylic acid moiety on each of the "B" and "C" aromatic rings of the MSTPM dye also can be used. Such complexones can be derived from common dyes such as cresolsulfonephthalein, phenolphthalein, phenolsulfonephthalein, bromophthalein, and similar phenolphthalein-type dyes and phenolsulfonephthalein-type dyes, and mixtures thereof. Other exemplary MSTPM dyes useful in the reagent composition include, but are not limited to, methylthymol blue, xylenol orange and thymolphthalein complexone.

MSTPM dyes, like cresolphthalein complexone, have been used at a pH of at least about 10 to detect serum calcium levels after diluting a test sample, like urine. However, the determination of serum calcium levels provides only an approximate correlation to urine specific gravity. In accordance with an important feature of the present invention, total urine divalent cation concentration, including both calcium and magnesium ions, is semiquantitatively correlated to urine specific gravity by utilizing a proper concentration of an MSTPM dye, and within a proper pH range. Using an MSTPM dye, within the above-disclosed concentration range and buffered at a pH in the range of about 7 to about 8, in a composition and method to assay for divalent cation concentration allows the semiquantitative assay for specific gravity to be performed without a dilution step. At a pH of about 8 or above, the composition and method can be used to assay for calcium ion concentration because, at this pH, the MSTPM dye selectively complexes with calcium ion and essentially does not complex with magnesium ions.

By buffering the reagent composition at a pH of about 7 to about 8, and by including a relatively high amount of the MSTPM dye in the reagent composition, the binding constant of the MSTPM dye is lowered, and the MSTPM dye is more responsive to divalent cation mixtures, and to higher magnesium and calcium concentrations, than an MSTPM dye under high pH (i.e., about 8 or above) and low MSTPM dye concentration conditions. The relatively low pH (i.e., pH 7 to about 10) and high concentration of MSTPM dye utilized in the present composition and method also reduce the extinction coefficient of the MSTPM dye to a sufficient level such that color transitions are readily detected and differentiated.

Any of various types of buffers can be used in the reagent composition of the present invention to provide a pH in the range of at least about 7, and preferably from about 7 to about 10. The function of the buffer is to maintain the reagent composition at a substantially constant pH to produce a color transition in the reagent composition because of the presence of divalent cations in the test sample, and to optimize the response of the MSTPM dye to the divalent cations.

The amount of buffer included in the reagent composition depends upon the nature of the test sample. The concentration of the buffer however usually is about 100 millimolar (mM) to about 600 millimolar, although in particular cases the concentration of the buffer can be above or below this range. The particular buffer used in the reagent composition depends upon, and varies with, the MSTPM dye included in the reagent composition. For optimum assay results, the pH of the reagent composition is maintained at a pH value of about 7 to about 8, and preferably in the range of about 7 to about 7.5, if the assay is designed to assay for total divalent cation concentration. The pH of the reagent composition is maintained at a pH value of about 8 to about 10, if the assay is designed to assay for calcium ion concentration.

Suitable buffers include, for example, but are not limited to, acetate; BICINE; phthalate, borate; trichloracetate; sulfosalicylate; phosphate; tartarate; citrate; succinate; maleic acid; 2,2-bis(hydroxymethyl)-2,2',2''-nitrilotriethanol; 3,3-dimethylglutaric acid; 3-N-morpholinopropanesulfonic acid (MOPS); malonic acid; 1,3-bis[tris(hydroxymethyl)methylamino]propane (Bis-TRIS); tris(hydroxymethyl)aminomethane (TRIS); tris(hydroxymethyl)aminomethane-maleic acid (TRIS-maleate); tris (hydroxymethyl)aminomethane-malonic acid (TRIS-malonate); 3-N-(trishydroxymethyl)methylamino-2-hydroxypropanesulfonic acid (TAPSO); 2-([tris (hydroxymethyl)methyl]amino)ethanesulfonic acid (TES); 1,4-piperazinebis(ethanesulfonic acid) (PIPES); 4-morpholinoethanesulfonic acid (MES); N-2-hydroxyethylpiperazine-N'-2-ethanesulfonic acid (HEPES); and other suitable buffers well known in the art, and mixtures thereof.

In addition to the MSTPM dye and the buffer, the reagent composition optionally can include a chelating agent to reduce development of an interfering background color and to allow the assay of calcium and magnesium cation concentrations above a predetermined concentration. In the absence of a chelating agent, the interaction between the reagent composition and the divalent cation components of the test sample can provide an interfering background color. In the absence of a chelating agent, all divalent cations interact with the MSPTM dye. Therefore, if divalent cation concentration is sufficiently high, too intense of a color transition, i.e., a nondifferentiable color transition, can result.

Therefore, a chelating agent, such as ethylenediaminetetraacetic acid (EDTA), optionally can be included in the reagent composition to preferentially interact with the divalent cations. Because divalent cations preferentially interact with the chelating agent as opposed to the MSTPM dye, a portion of the divalent cations in the test sample are not available to interact with the MSTPM dye. However, divalent cations present in excess of the concentration of chelating agent in the reagent composition are available to interact with the MSTPM dye to provide a detectable and differentiable color transition. If the divalent cation concentration of a test samples is sufficiently low, a chelating agent is not needed and may adversely affect an assay for divalent cation concentration or specific gravity.

Incorporating a chelating agent into the reagent composition therefore facilitates the assay for divalent cation concentration in a test sample having a relatively high divalent cation concentration. The color transition of the reagent composition is a result of an interaction between the MSTPM dye and the divalent cation concentration in excess of the chelating agent concentration. Since the chelating agent concentration is known, the divalent cation concentration can be determined from comparing the color transition of the test sample to the color transition provided by standard samples including divalent cations. This color transition also can be correlated, semiquantitatively, to test sample specific gravity.

The optional chelating agent utilized in the present invention is not particularly limited. However, an organic chelating agent, like a chelating dicarboxylic or polycarboxylic acid, or like the polycarboxyalkylamine chelating agents, such as ethylenediaminetetraacetic acid, is most preferably employed. Other classes of useful chelating agents include, but are not limited to, a polyhydroxy compound, like sorbitol; a lignosulfonate; a glucoheptonate; dimethylglyoxime; salicylate complexes, like bissalicylaldehydeethylenediimine; dithionate derivatives; polyethyleneamines, like triethyleneamine; a 2,4-pentanedione derivative; a dipyridine derivative; triethylenepyridine amine; a polypeptide containing cysteine, glycine or histidine; a proline derivative; a thiocrown ether, like 1,4,8,11,22,25-octathiacyclooctosane; a triphenylphosphine; or mixtures thereof.

Particular examples of optional chelating agents useful in the reagent composition of the present invention include, but are not limited to, tartaric acid, oxalic acid, malonic acid, succinic acid, citric acid, ethylenediaminetetraacetic acid (EDTA), gluconic acid, N-(hydroxyethyl)ethylenediaminetriacetic acid (HEDTA), nitrilotriacetic acid (NTA), diethylenetriaminepentaacetic acid (DTPA), aminotris(methylene phosphoric acid), hydroxyethylidene diphosphonic acid, hexamethylenediaminetetra(methylene phosphonate), ethylenediaminediacetic acid (EDDA), iminodiacetic acid (IDA), nitrilopropionic acid (NTP), hydroxyethyliminodiacetic acid (HIDA), pyrophosphoric acid, 1-hydroxyethane-1,1-diphosphonic acid, tripolyphosphoric acid, hexametaphosphoric acid, and metaphosphoric acid; or mixtures thereof.

The optional chelating agent can be added to the reagent composition in the free acid form, or in the form of a water-soluble salt, such as the sodium, potassium, lithium, ammonium, alkyl-substituted ammonium or hydroxyalkyl-substituted ammonium salt. The chelating agent is included in the reagent composition in a concentration of 0 mM to about 5 mM, and preferably of about 0.5 mM to about 4 mM. Within this range, the chelating agent is present in sufficient quantity to chelate a portion of the divalent cations, while the remaining portion of the divalent cations is available to interact with the MSTPM dye and provide an assay for specific gravity or divalent cation concentration or specific gravity from the resulting color transition.

In addition to the above-described ingredients, other optional ingredients that do not materially alter the nature or the function of the reagent composition, and that do not interfere with the assay for divalent cations or specific gravity, also can be included in the reagent composition. For example, the reagent composition optionally can include a compound to improve the wetting of the test pad of the test device by the test sample. This compound usually is an anionic surfactant or a nonionic surfactant. A nonionic surfactant, such as an octoxynol, a nonoxynol or an ethoxylated fatty alcohol, is the preferred surfactant. An anionic surfactant, such as a long carbon chain sulfate or sulfonate, like sodium dodecyl sulfate, dioctyl sodium sulfosuccinate and sodium dodecylbenzene sulphonate, also can be included in the reagent composition of the present invention. The surfactant is included in the indicator reagent composition in a concentration of 0 mM to about 200 mM, and preferably in a concentration of about 50 mM to about 200 mM.

The reagent composition also can include a polymeric material that improves the stability and uniformity of the color transition of the test device. Suitable polymeric materials include, but are not limited to, Polyvinylpyrrolidone, polyvinylalcohol, gum arabic, gelatin, algin, carrageenan, casein, albumin, methylcellulose and similar natural and synthetic polymeric materials. The preferred polymeric material is a polyvinylpyrrolidone of average molecular weight 40,000 and available commercially from GAF Corp., New York, N.Y. The polymeric material generally is included in the reagent composition in an amount of 0% to about 5%, and preferably about 0% to about 4%, by total weight of the reagent composition.

The carrier for the ingredients included in the reagent composition is predominantly water. However, because of the limited water solubility of particular ingredients included in the indicator reagent composition, organic solvents such as methanol, ethanol, isopropyl alcohol, ethylene glycol, propylene glycol, acetone, dimethylformamide, dimethylsulfoxide, acetonitrile, ethyl acetate and similar solvents can be included in the carrier. The selection of a suitable organic solvent or solvents, in addition to water, to include in the carrier of the reagent composition is within the capability of those skilled in the art of designing diagnostic assays.

The amount of organic solvent present in the indicator reagent composition generally is 0% to about 20%, and preferably about 0% to about 10%, by weight of the carrier. A carrier solvent comprising water and an organic solvent, like methanol or ethanol, is especially preferred because a carrier matrix impregnated with the indicator reagent composition can be dried within a few to several minutes.

As previously described, the reagent composition undergoes a color transition upon contact with a test sample to demonstrate the presence of divalent cations, and provide an assay for divalent cation concentration or test sample specific gravity. The intensity and degree of the color transition are used either to quantitatively determine divalent cation concentration or to semiquantitatively determine specific gravity. In accordance with an important feature of the present invention, a reagent composition of the present invention provides a sufficiently resolved and differentiated color transition such that the divalent cation concentration of a test sample can be measured and accurately determined without the use of color-measuring instruments, such as spectrophotometers or colorimeters. However, if desired, such color-measuring instruments can be used to measure the difference in color degree and intensity between the test sample and a solution having a known concentration of divalent cations.

Upon contact with the urine or other aqueous test sample, the MSTPM dye of the reagent composition interacts with uncomplexed divalent cations and undergoes a color transition that is correlated to the divalent cation concentration of the test sample. Because divalent cation concentration is directly proportional to specific gravity, the color transition also can be correlated, semiquantitatively, to test sample specific gravity. The intensity and degree of the color transition are used to determine the divalent cation concentration or specific gravity of the test sample by comparing or correlating the color produced by the test sample to colors produced by solutions having a known divalent cation concentration or a known specific gravity. In accordance with an important feature of the present invention, the reagent composition provides a sufficiently resolved and differentiated color transition such that the divalent cation concentration, or the specific gravity, of the test sample can be measured without the use of color-measuring instruments.

Accordingly, the method of the present invention, utilizing a reagent composition including a MSTPM dye, a buffer, an optional chelating agent and a suitable carrier, improves the accuracy and reliability of the divalent cation concentration assay, and also increases physician confidence in the divalent cation concentration assay. The method also provides a semiquantitative assay for specific gravity of a test liquid. Because of the number of urine assays for specific gravity being performed at home by untrained individuals, as opposed to trained physicians or technicians in the laboratory, it is imperative to provide a fast and reliable semiquantitative assay method for the specific gravity of urine that can be used in conjunction with assays for other urine constituents.

Conventionally, assays for specific gravity have been conducted at an essentially neutral pH using an indicator dye that undergoes a color transition at an essentially neutral pH in response to a $pK_a$ change and a pH decrease in a polyelectrolyte. In accordance with the method and composition of the present invention, specific gravity is determined semiquantitatively in the absence of a polyelectrolyte, wherein divalent cations present in the test sample interact directly with an MSTPM dye, and cause a color transition. The degree and intensity of the color transition are directly related to the specific gravity, and to the divalent cation concentration, of the test sample. The specific gravity reagent composition is adjusted to and maintained at pH in the range of about 7 to about 8. Within this pH range, the pH is sufficiently high to provide a detectable and differentiable response to the MSTPM dye-divalent cation interaction, and is sufficiently low for the MSTPM dye to interact with both calcium and magnesium ions, and therefore provide a more accurate specific gravity assay.

To demonstrate the new and unexpected results achieved by the method and composition of the present invention, a reagent composition, including cresolphthalein complexone as the MSTPM dye, was prepared, then used in a dry phase assay for the specific gravity of a test sample. In addition to the cresolphthalein complexone, the reagent composition included 3-N-morpholinopropanesulfonic acid (MOPS) to buffer the reagent composition at a pH of about 7.25. In one embodiment, the reagent composition included ethylenediaminetetraacetic acid (EDTA) as the chelating agent; in an alternate embodiment, the reagent composition did not include a chelating agent.

The aqueous solution of the cresolphthalein complexone, MOPS buffer, and, if present, EDTA is colorless and, after incorporation into a suitable carrier matrix changes color ranging from colorless to deep purple after contact and interaction with test samples having an increasing divalent cation concentration or specific gravity. As a result, a reagent composition including suitable amounts of an MSTPM dye, like cresolphthalein complexone; and a chelating agent, if desired, like EDTA; adjusted to and maintained at a suitable pH of about 7 to about 8 with a suitable buffer, after incorporation into a suitable carrier matrix, produced the color transitions summarized in TABLE I upon contact and interaction with solutions including different calcium ion concentrations. The range of calcium ion concentrations (0–10 mM) covers the concentration of calcium ions usually found in urine.

TABLE I

COLOR TRANSITION OF REAGENT COMPOSITION INCLUDING BUFFERED CRESOLPHTHALEIN COMPLEXONE UPON INTERACTION WITH SOLUTIONS INCLUDING CALCIUM IONS (pH = 7.25)

| Calcium Concentration (mM) | Observed Color |
| --- | --- |
| 0 | colorless |
| 2 | slightly purple |
| 5 | red-purple |
| 10 | deep purple |

In accordance with an important feature of the present invention, the color resolution achieved using the present reagent composition permits not only measurement of divalent cation concentration (e.g., calcium ion concentration), but also permits differentiation between test samples having different specific gravities.

To perform a dry phase, test strip assay for divalent cation concentration or specific gravity, the reagent composition is produced first. For example, a reagent composition is produced by simply admixing the composition ingredients to provide an aqueous, alcoholic or hydroalcoholic solution that is 0.2M (molar) in MOPS (adjusted to pH 7.25); 20 mM (millimolar) in cresolphthalein complexone; and 2 mM EDTA. The MOPS was added to the reagent composition to serve as a buffer and the EDTA was added to serve as a chelating agent.

A reagent composition including the buffered MSTPM dye as described above can be used in dry phase, test pad assays for divalent cation concentration or for specific gravity. A dry phase, test pad assay for specific gravity that utilizes the reagent composition is performed in accordance with methods well known in the art. In general, the assay for divalent cation concentration or specific gravity is performed by contacting the urine or other test sample with an analyte detection device that includes the reagent composition. The analyte detection device can be dipped into the test sample, or the test sample can be applied to the analyte detection device dropwise. The resulting change in color of the analyte detection device reveals the divalent cation concentration or the specific gravity, of the test sample; and, if so designed, the resulting color transition can be compared to a standardized color chart to provide a measurement of the divalent cation concentration or specific gravity of the urine or test sample.

Typically, the analyte detection device is a test strip impregnated with a reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move, in response to capillary forces, through the matrix to contact the reagent composition and produce a detectable and measurable color transition.

The carrier matrix can be any substance capable of incorporating the chemical reagents required to perform the assay of interest, as long as the carrier matrix is substantially inert with respect to the chemical reagents and does not contaminate the urine or other test samples either by test sample extraction of components comprising the carrier matrix or by appreciably altering the urine or test sample in a way to make the subsequent assays inconclusive, inaccurate or doubtful. The carrier matrix also is porous or absorbent relative to the liquid test sample.

The expression "carrier matrix" refers either to bibulous or nonbibulous matrices that are insoluble in water and other physiological fluids and that maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally-occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate or polystyrene, and the carrier matrix is most advantageously constructed from filter paper or polymeric films.

To achieve the full advantage of the present invention, the present reagent composition is incorporated into a suitable carrier matrix to provide a test pad, and the test pad is utilized in a dry phase test strip for the divalent cation concentration or specific gravity assay of an aqueous test sample. The method of the present invention provides an economical, accurate and reliable assay of aqueous test samples that can be performed at home or in the laboratory. In addition, the method of the present invention allows the differentiation and measurement of test sample divalent cation concentration or specific gravity, therefore making the method and composition more useful clinically.

In accordance with the method of the present invention, to perform a dry phase, test strip assay for divalent cation concentration or specific gravity, the aqueous reagent composition described above, including about 5 mM to about 60 mM of an MSTPM dye, such as cresolphthalein complexone; 100 mM to about 600 mM of a buffer, such as MOPS; and 0 mM to about 5 mM of a chelating agent like EDTA, adjusted to and buffered at a pH of about 7 to about 8, first is prepared. A bibulous matrix, such as filter paper, like WHATMAN CCP500 filter paper, available commercially from Whatman Ltd., Maidstone, Kent, U.K., then is saturated and impregnated with the aqueous solution of the reagent composition containing the buffered MSTPM dye and the chelating agent either by spreading, by immersing or by spraying the aqueous solution onto sheets of precut strips of the filter paper. After removing the aqueous solvent by oven drying in an air oven at about 50° C. for about 15 to 20 minutes, the filter paper incorporating the reagent composition is cut to an appropriate size, such as a pad having dimensions from about 0.25 cm by about 0.25 cm to about 1.0 cm by about 1.0 cm. The filter paper incorporating the reagent composition then is secured to an opaque or transparent hydrophobic plastic handle with double sided adhesive tape.

The resulting test strip then was dipped into a fresh, uncentrifuged urine sample for a sufficient time to saturate the test pad with the sample. After waiting a predetermined time, such as from about one minute to about two minutes, the test strip is examined, either visually or instrumentally, for a response. The degree and intensity of the color transition of the test pad reveal the divalent cation concentration, or, if desired, the specific gravity, of the urine sample.

In accordance with another important feature of the present invention, it is well within the experimental techniques of those skilled in the art of preparing test devices to determine the proper balance between size of test pad; the strength of reagent composition; the identity and amount of MSTPM dye, chelating agent and buffer in the reagent composition; the amount of test sample; and the method of introducing the test sample to the test strip, such as by pipetting rather than dipping, to provide detectable and differentiable color transitions, such that a comparison, either visually or instrumentally, to color standards derived from solutions of known divalent cation concentration or specific gravity is possible.

In many cases simple visual observation of the test strip provides the desired information. If more accurate information is required, a color chart bearing color spots corresponding to various standard divalent cation concentrations or specific gravities can be prepared for the particular MSTPM dye reagent composition used in the test strip. The resulting color of the test strip after contact with the urine sample then can be compared with the color spots on the chart to determine the divalent cation concentration or specific gravity of the test sample.

If a still more accurate determination is required, a spectrophotometer or colorimeter can be used to more precisely determine the degree and intensity of the color transition. In addition, the dry phase, reagent strip assay can be made quantitative by employing spectrophotometric or colorimetric techniques, as opposed to visual techniques, in order to more reliably and more accurately measure the degree and intensity of color transition, and therefore more accurately measure the divalent cation concentration or specific gravity of the test sample.

To show the new and unexpected results arising from using the reagent composition of the present invention to differentiate and measure the divalent cation concentration or specific gravity of a test sample, color space plots were prepared from assays using dry phase test strips having a test pad incorporating a reagent composition including a MSTPM dye into a filter paper matrix. The color space plots were obtained by contacting standardized solutions of known divalent cation concentration or specific gravity with the dry phase test strips including the present reagent composition incorporated into a filter paper carrier matrix.

In general, a color space plot includes three axes, the L*, A* and B* axes. The values of L* plotted on the vertical axis are a measure of the intensity of color, whereby a large L* value denotes a light color and L*=0 denotes a completely black color. The horizontal A* axis is a measure of the color transition from green to red, whereby the more positive the A* value, the more red the color, and analogously, the more negative the A value, the more green the color. Similarly, the third axis, B*, is a measure of the color transition from blue to yellow, whereby the greater the value of B*, the more yellow the color, and analogously the smaller the value of B*, the more blue the color.

The color space difference ($\Delta E$) is calculated from the following equation (Eq. 2):

$$\Delta E = \sqrt{(L_1^* - L_2^*)^2 + (A_1^* - A_2^*)^2 + (B_1^* - B_2^*)^2} \qquad \text{Eq. 2}$$

wherein:

$L_1^*$, $A_1^*$, and $B_1^*$ are the color space values determined for a first standardized solution of known specific gravity or divalent cation concentration;

$L_2^*$, $A_2^*$ and $B_2^*$ are the color space values determined for a second standardized solution of known specific gravity or divalent cation concentration having a different specific gravity or divalent cation concentration from the first standardized solution; and $\Delta E$ is the color space difference between the color space plots of the first and second standardized solutions.

The color space difference ($\Delta E$) is the straight line distance between two points in a three-dimensional color space plot. Theoretically, a color space difference of one (1) unit is the smallest color difference the human eye can distinguish. However, because of the inherent differences between the visual capabilities of individuals, a color space difference ($\Delta E$) of about 3 units is required in order to practically and confidently distinguish between colors.

The L*, A* and B* values plotted on the color space plots are calculated from the different reflectance measurements taken at sixteen different wavelengths evenly spaced between 400 run (nanometers) and 700 nm using standard equations well-known in the art. In general, the percent reflectance at each of the sixteen different wavelengths is multiplied by the intensity of the light at that wavelength. These values then are multiplied by standard weighing functions for the colors red, green and blue, and finally added together. These calculations yield three tristimulus values, X, Y and Z. L*, A* and B* are calculated from the X, Y and Z tristimulus values using the following equations:

$$L^* = 116 \times [(Y/Y_o)^{\frac{1}{3}} - 16)] \quad \text{(Eq. 3)}$$

$$A^* = 500 \times [(X/X_o)^{\frac{1}{3}} - (Y/Y_o)^{\frac{1}{3}}] \quad \text{(Eq. 4)}$$

$$B^* = 200 \times [(Y/Y_o)^{\frac{1}{3}} - (Z/Z_o)^{\frac{1}{3}}] \quad \text{(Eq. 5)}$$

wherein:

$X_o$, $Y_o$ and $Z_o$ are the tristimulus values for perfect white (i.e., reflectance=100% at all wavelengths), and X, Y and Z are the tristimulus values calculated as described above from the sixteen wavelengths between 400 nm and 700 nm.

From the color space plots, the color space differences (ΔE) were calculated, and are summarized and discussed in more detail hereinafter. In interpreting the data to be presented, a term such as ΔE (1.007–1.022) is the color space difference between specific gravity assays for standardized urine solutions having a specific gravity of 1.007 and 1.022. Similarly, the term ΔE (0–0.5) is the color space difference between assays of standardized solutions having a calcium chloride, i.e., divalent cation, concentration of 0 mM and 0.5 mM respectively. The terms ΔE (0.5–2) and ΔE (2–10) are analogously defined.

To demonstrate the unexpected results provided by a reagent composition of the present invention, two sets of test strips were prepared, then used to assay for divalent cation concentration and specific gravity of a test sample. Both sets of test strips utilized filter paper (WHATMAN CCP500) as the carrier matrix of the test pad. In Test Strips A, an aqueous solution of pH about 7.25 and including 20 mM cresolphthalein complexone and 0.2M MOPS was incorporated into the filter paper matrix. In Test Strips B, an aqueous solution of pH about 7.25 and including 20 mM cresolphthalein complexone, 0.2M MOPS and 2 mM EDTA was incorporated into the filter paper matrix.

The compositions incorporated into Test Strips A and Test Strips B each are compositions of the present invention. The composition incorporated into Test Strips A does not include a chelating agent, and therefore is more sensitive to low concentrations of divalent cations than the composition incorporated into Test Strips B. Test Strips B demonstrate a sensitivity to divalent cations above a concentration of 2 mM, i.e., above the concentration of the chelating agent.

Individual Test Strips A and Test Strips B were dipped into standardized calcium chloride solutions including 0, 0.5, 2 and 10 mM calcium chloride and into standardized urine solutions having a specific gravity of 1.007 to 1.022. The resulting color transition of each test strip was determined and converted into ΔE units by standard procedures known in the art. The ΔE units for these experiments are summarized in TABLE II.

TABLE II

| | ΔE DIFFERENCES FOR ASSAYS UTILIZING A BUFFERED MSTPM DYE | | | |
|---|---|---|---|---|
| Test Strips | CaCl₂ Concentration (mM) | | | Urine Specific Gravity |
| | ΔE (0–0.5) | ΔE (0.5–2) | ΔE (2–10) | ΔE (1.007–1.022) |
| A | 3 | 11 | 31 | 9.4 |

TABLE II-continued

| | ΔE DIFFERENCES FOR ASSAYS UTILIZING A BUFFERED MSTPM DYE | | | |
|---|---|---|---|---|
| Test Strips | CaCl₂ Concentration (mM) | | | Urine Specific Gravity |
| | ΔE (0–0.5) | ΔE (0.5–2) | ΔE (2–10) | ΔE (1.007–1.022) |
| B | 0 | 4 | 39 | 12 |

In accordance with the method and composition of the present invention, from TABLE II, using the MSTPM dye in a reagent composition to assay for divalent cation concentration or specific gravity, the color space differences are near or above the minimum human detectable limit of approximately three ΔE units, thereby providing a divalent cation concentration assay or specific gravity assay of the test sample. Generally, the color space difference values are at or above 3, therefore a color change is discernible by the human eye, and the assayer easily can differentiate between urine samples having different divalent cation concentrations or specific gravities.

Specifically, Test Strips A, including a reagent composition absent a chelating agent, showed a sensitivity to calcium ions in the range of 0 mM to 0.5 mM that is perceptible to the human eye. Test Strips A showed a readily perceptible sensitivity to calcium ions in the range of 0.5 mM to 2 mM and in the range of mM to 10 mM, thereby allowing an assayer to distinguish between test samples including 0.5 mM, 2 mM or 10 mM calcium ions. Similarly, an assayer can easily distinguish between a urine sample having a specific gravity of 1.007 and a sample having a specific gravity of 1,022 because the color space difference (ΔE) is a readily perceptible 9.4 units.

Test Strips B, incorporating a reagent composition including 2 mM of the chelating agent EDTA, are not sensitive to calcium ions present in a concentration of about 0.5 mM or less, and are marginally sensitive to calcium ions present in a concentration of about 0.5 mM to about 2 mM, as demonstrated by the ΔE (0.5–2) value for calcium ion of 4, compared to the ΔE (0–0.5) value for calcium ion of 0. The calcium ions in this concentration range preferably complex with the EDTA. The calcium ions in excess of about 2 mM are available to interact with the MSTPM dye and cause a color transition, as demonstrated by the ΔE (2–10) value for calcium ion of 39.

It also should be noted that the ΔE (1.007–1.022) value (i.e., 12) in the specific gravity assay using Test Strips B was greater than the ΔE (1,007–1,022) value (i.e., 9.4) using Test Strips A. This greater ΔE value translates into a more easily differentiable color transition. The more differentiable color transition is attributed to the chelating agent suppressing the development of an interfering background color in the test pad. By chelating a portion of the divalent cations in the test sample, a lower concentration of divalent cations is available to interact with the MSTPM dye. Accordingly, the color transition is less intense. This less intense color transition allows a greater differentiation between color transition because as the concentration of divalent cations in a test sample increases, the resulting color transition is compared to a substantially less intense color transition, thereby providing a larger ΔE value.

As a result, using an MSTPM dye in a reagent composition as an indicator to differentiate and measure the divalent cation concentration and the specific gravity of a test sample, allows the accurate and reliable divalent cation concentration and specific gravity determination of test samples. The present reagent compositions provide an important and useful benefit of substantially reducing the development of a background color compared to compositions that relied upon the pK$_a$ change of a polyelectrolyte to assay for the specific gravity of test samples. As illustrated above, the MSTPM dye included in the present composition responds directly to the divalent cation concentration of the test sample, and provides an accurate divalent cation concentration assay and a semiquantitative specific gravity assay.

It should be understood that those skilled in the art of designing test kits are able to design an optimal test strip incorporating a sufficient amount of a particularly effective reagent composition to permit the differentiation and measurement of test sample divalent cation concentrations and specific gravities because an assay utilizing the method and composition of the present invention exhibits a color space difference of at least 3 units. This ΔE value is sufficient for detection by the human eye, and is easily detected by present day colorimeters or spectrophotometers. Similarly, the method and composition of the present invention provide an accurate divalent cation concentration assay or semiquantitative specific gravity assay regardless of varying amounts of nonionic components, such as glucose or albumin, found in the test sample, as long as sufficient divalent cations are present in the zest sample to cause a color transition.

In accordance with another important feature of the present invention, full color development of a test strip including an MSTPM dye in the reagent composition occurs within about one minute to about two minutes after contacting the test strip with the test sample. Maximum color development occurs after about two minutes of contact. However, acceptable and trustworthy assay results are achieved when the test strip is examined for a color change about one minute after contact with the test sample. Such a short time for full color development of the test strip is an additional advantage of the reagent composition of the present invention. In addition, the color transition is sufficiently stable such that an accurate assay results from examining the test strip up to ten minutes after contacting the test sample. Therefore, test strips incorporating the reagent composition of the present invention can be used to obtain fast and accurate divalent concentration assays and semiquantitative specific gravity assays.

Overall, a buffered MSTPM dye included in a reagent composition incorporated into a suitable carrier matrix, such as filter paper, improves color differentiation between test samples having sufficiently different specific gravities and provides excellent sensitivity to the divalent cation concentration of aqueous test samples. In addition to excellent sensitivity, the method and composition of the present invention substantially reduce the development of an interfering background color, and provide full color development and accurate assay results in a relatively short time.

Therefore, in accordance with an important feature of the present invention, accurate and reliable assays for the divalent cation concentration and semiquantitative assay for the specific gravity of urine and other liquid test samples can be performed by utilizing a MSTPM dye, a buffer and, if desired, a chelating agent in a reagent composition. The MSTPM dye provides sufficient color differentiation between test samples having different divalent cation concentrations and specific gravities, and therefore provides sufficient assay sensitivity.

Obviously, many modifications and variations of the invention as hereinbefore set forth can be made without departing from the spirit and scope thereof and therefore only such limitations should be imposed as are indicated by the appended claims.

What is claimed is:

1. A composition capable of exhibiting a detectable and measurable color transition only in response to a total divalent cation concentration of an aqueous test sample, said composition comprising:

(a) about 5 to about 60 millimoles per liter of the composition of a metal-sensitive triphenylmethane dye having the structural formula:

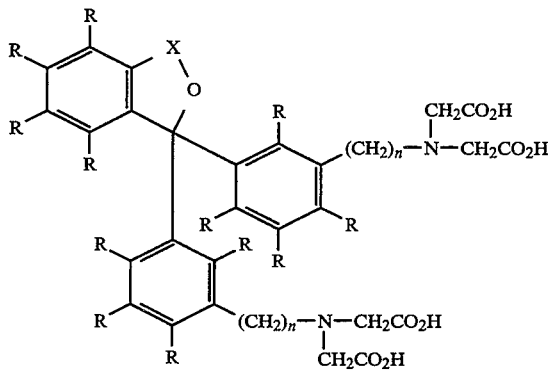

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;

(b) a buffer;

(c) a carrier comprising water; and (d) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bissalicylaldehydeethylenediimine, triethyleneamine, triethylenepyridine amine, 1,4,8,11,22,25-octathiacyclooctosane, ethylenediaminetetraacetic acid, N-(hydroxyethyl) ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof;

wherein the composition is buffered at a pH of at least about 7.

2. The composition of claim 1 wherein the metal-sensitive triphenylmethane dye is selected from the group consisting of cresolphthalein complexone, cresolsulfonephthalein complexone, phenolphthalein complexone, phenolsulfonephthalein complexone, bromophthalein complexone, methylthymol blue, xylenol orange, thymolphthalein complexone and mixtures thereof.

3. The composition of claim 1 wherein the buffer is present in a concentration of about 100 to about 600 millimoles per liter of the composition.

4. The composition of claim 1 wherein the composition is buffered at a pH of at least about 7 to about 10.

5. The composition of claim 1 wherein the buffer is selected from the group consisting of acetate; BICINE; phthalate; borate; trichloracetate; sulfosalicylate; phosphate; tartarate; citrate; succinate; maleic acid; 2,2-bis(-hydroxymethyl)-2,2',2''-nitrilotriethanol; 3,3-dimethylglutaric acid; 3-N-morpholinopropanesulfonic acid; malonic acid; 1,3-bis[tris(hydroxymethyl)methylamino]propane; tris(hydroxymethyl)aminomethane; tris(hydroxymethyl)aminomethane-maleic acid; tris(hydroxymethyl)aminomethane-malonic acid; 3-N-(trishydroxymethyl)methylamino-2-hydroxypropanesulfonic acid; 2-([tris(hydroxymethyl)methyl]amino)-ethanesulfonic acid; 1,4-piperazinebis(ethanesulfonic acid); 4-morpholinoethanesulfonic acid; N-2-hydroxyethylpiperazine-N'-2-ethanesulfonic acid; and mixtures thereof.

6. The composition of claim 1 wherein the carrier further comprises 0% to about 20% by weight of an organic solvent, based on the weight of the carrier.

7. A method of determining a total divalent cation concentration of an aqueous test sample comprising:
   (a) contacting the aqueous test sample with a reagent composition capable of exhibiting a color transition only in response to the total divalent cation concentration of the aqueous test sample, said composition comprising:
      (i) about 5 to about 60 millimoles per liter of the composition of a metal-sensitive triphenylmethane dye having the structural formula:

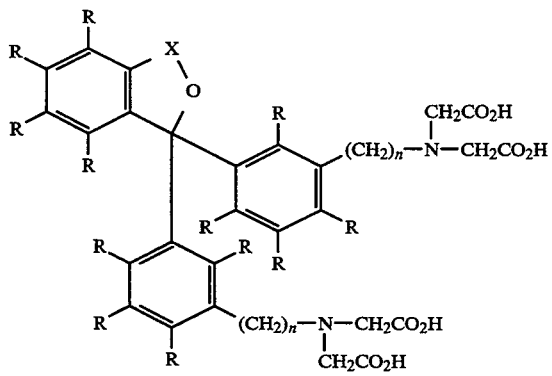

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;
      (ii) a buffer;
      (iii) a carrier comprising water; and
      (iv) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bissalicylaldehydeethylenediimine, triethyleneamine, triethylenepyridine amine, 1,4,8,11,22,25-octathiacyclooctosane, ethylenediaminetetraacetic acid, N-(hydroxyethyl)ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof, wherein the reagent composition is buffered to a pH of about 7 to about 8; and
   (b) determining the total divalent cation concentration of the aqueous test sample from the intensity and degree of the color transition of the reagent composition.

8. The method of claim 7 wherein the aqueous test sample is a biological fluid.

9. The method of claim 8 wherein the biological fluid is selected from the group consisting of urine, blood plasma, blood serum, and perspiration.

10. The method of claim 7 wherein the buffer is present in a concentration of about 100 to about 600 millimoles per liter of the composition.

11. The method of claim 7 wherein the carrier further comprises 0% to about 20% by weight of an organic solvent based on the weight of the carrier.

12. The method of claim 7 wherein the intensity and degree of the color transition is determined visually or instrumentally.

13. A method of semiquantitatively determining a specific gravity of an aqueous solution comprising:
   (a) contacting the aqueous solution with a reagent composition capable of measuring the total divalent cation concentration of the aqueous solution, said composition comprising:
      (i) about 5 to about 60 millimoles per liter of the composition of a metal-sensitive triphenylmethane dye having the structural formula:

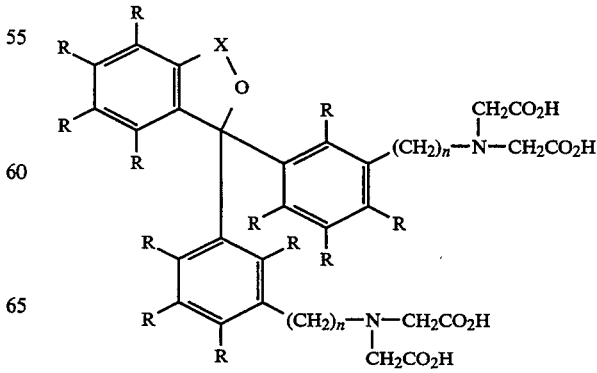

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;

(ii) a buffer;

(iii) a carrier comprising water; and (iv) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bissalicylaldehydeethylenediimine, triethyleneamine, triethylenepyridine amine, 1,4,8,11,22,25-octathiacyclooctosane, ethylenediaminetetraacetic acid, N-(hydroxyethyl)ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof, wherein the reagent composition is buffered to a pH of about 7;

(b) determining the total divalent cation concentration of the aqueous solution from the intensity and degree of the color transition of the reagent composition, wherein the color transition is in response only to the total divalent cation concentration of the aqueous solution; and (c) correlating the total divalent cation concentration of the aqueous solution to the specific gravity of the aqueous solution.

14. The method of claim 13 wherein the aqueous solution is a biological fluid.

15. The method of claim 14 wherein the biological fluid is selected from the group consisting of urine, blood plasma, blood serum, and perspiration.

16. A method of determining a total divalent cation concentration of an aqueous sample comprising:

(a) contacting the aqueous sample with an analyte detection device comprising a test pad, said test pad having incorporated therein a reagent composition capable of exhibiting a color transition only in response to the total divalent cation concentration of the aqueous sample, said composition comprising:

(i) about 5 to about 60 millimoles per liter of the composition of a metal-sensitive triphenylmethane dye having the structural formula:

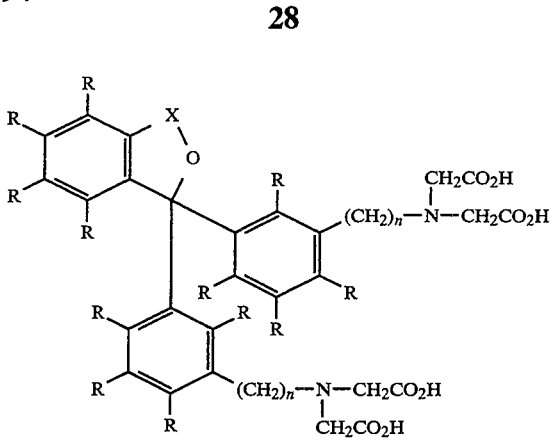

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;

(ii) a buffer;

(iii) a carrier comprising water; and (iv) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bissalicylaldehydeethylenediimine, triethyleneamine, triethylenepyridine amine, 1,4,8,11,22,25-octathiacyclooctosane, ethylenediaminetetraacetic acid, N-(hydroxyethyl)ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof, wherein the reagent composition is buffered to a pH of about 7, and (b) determining the total divalent cation concentration of the aqueous sample from the intensity and degree of the color transition of the reagent composition.

17. A method of semiquantitatively determining a specific gravity of an aqueous divalent cation-containing sample comprising:

(a) contacting the aqueous sample with an analyte detection device comprising a test pad having incorporated therein a composition capable of undergoing a color transition only in response to the total divalent cation concentration of the aqueous sample, said composition comprising:

(i) about 5 to about 60 millimoles per liter of the composition of a metal-sensitive triphenylmethane dye having the structural formula:

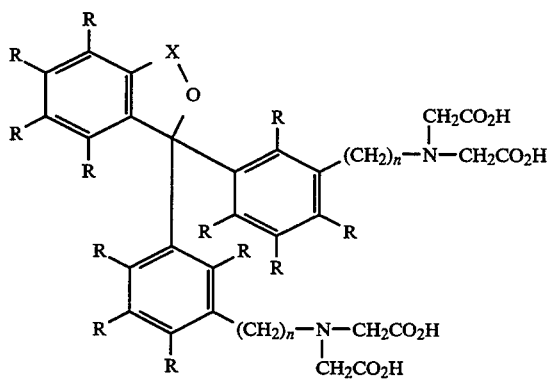

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;

(ii) a buffer;

(iii) a carrier comprising water; and (iv) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bis-salicylaldehydeethylenediimine, triethyleneamine, triethylenepyridine amine, 1,4,8,11,22,25-octathiacyclooctosane, ethylenediaminetetraacetic acid, N-(hydroxyethyl)ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof, wherein the reagent composition is buffered to a pH of about 7, and (b) examining the analyte detection device for a color transition in response only to the total divalent cation content of the aqueous sample; and (c) correlating the color transition to the specific gravity of the aqueous sample.

18. The method of claim 17 wherein the aqueous sample has a specific gravity of about 1.000 to about 1.015.

19. An analyte detection device to determine a total divalent cation concentration of an aqueous test sample comprising:

a support strip;
a test pad; and
a reagent composition incorporated into the test pad, said reagent composition capable of undergoing a color transition only in response to the total divalent cation concentration of the aqueous sample and said reagent composition comprising:

(a) about 5 to about 60 millimoles per liter of the composition of a metal-sensitive triphenylmethane dye having the structural formula:

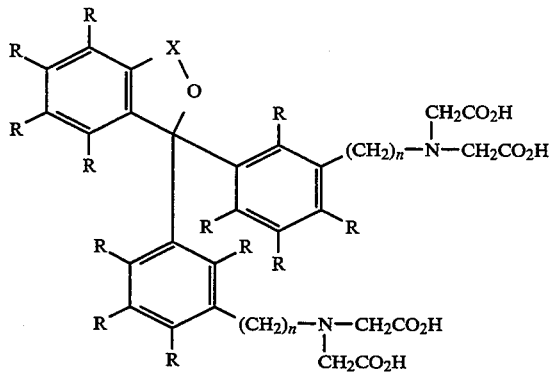

wherein X is carbonyl or sulfonyl, n is a number from 0 to about 3, and the R substituents are selected, independently, from the group consisting of hydrogen, hydroxy, an alkyl group including one to about five carbon atoms, bromo, chloro, fluoro, iodo, sulfonate, and phosphate;

(b) a buffer;

(c) a carrier comprising water; and (d) about 0.5 to about 4 millimoles per liter of the composition of a chelating agent selected from the group consisting of a polyhydroxy compound, a lignosulfonate, a glucoheptonate, a salicyate complex, a dithionate derivative, a polyethyleneamine, a 2,4-pentanedione, a dipyridine, a polypeptide including cysteine, glycine or histidine, a thiocrown ether, a triphenylphosphine, sorbitol, dimethylglyoxime, proline, bis-salicylaldehydeethylenediimine, triethyleneamine, triethylenepyridine amine, 1,4,8,11,22,25-octathiacyclooctosane, ethylenediaminetetraacetic acid, N-hydroxyethyl)ethylenediaminetriacetic acid, nitrilotriacetic acid, diethylenetriaminepentaacetic acid, aminotris(methylene phosphoric acid), hydroxyethylidene diphosphonic acid, hexamethylenediaminetetra(methylene phosphonate), ethylenediaminediacetic acid, iminodiacetic acid, nitrilopropionic acid, hydroxyethyliminodiacetic acid, pyrophosphoric acid, 1-hydroxyethane-1,1-diphosphonic acid, tripolyphosphoric acid, hexametaphosphoric acid, metaphosphoric acid, and mixtures thereof, wherein the reagent composition is buffered at a pH of at least about 7.

* * * * *